United States Patent
Filipi et al.

(10) Patent No.: US 8,820,320 B2
(45) Date of Patent: Sep. 2, 2014

(54) BITE BLOCKS

(75) Inventors: Charles J. Filipi, Omaha, NE (US); Michael L. Hadley, Mesa, AZ (US)

(73) Assignee: Creighton University, Omaha, NE (US)

( * ) Notice: Subject to any disclaimer, the term of this patent is extended or adjusted under 35 U.S.C. 154(b) by 1122 days.

(21) Appl. No.: 12/623,882

(22) Filed: Nov. 23, 2009

(65) Prior Publication Data
US 2010/0132700 A1 Jun. 3, 2010

Related U.S. Application Data

(63) Continuation of application No. PCT/US2008/064438, filed on May 21, 2008.

(60) Provisional application No. 60/939,348, filed on May 21, 2007.

(51) Int. Cl.
*A61M 11/00* (2006.01)

(52) U.S. Cl.
USPC .................. 128/200.26; 606/108; 600/237

(58) Field of Classification Search
USPC .................. 128/200.26, 207.17, 207.14; 600/237–240; 606/108
See application file for complete search history.

(56) References Cited

U.S. PATENT DOCUMENTS

| | | |
|---|---|---|
| 2,908,269 A | 3/1958 | Cheng |
| 3,756,244 A | 9/1973 | Kinnear |
| 3,774,616 A | 11/1973 | White et al. |
| 4,166,467 A | 9/1979 | Abramson |
| 4,214,594 A | 7/1980 | Little |
| 4,235,229 A | 11/1980 | Ranford et al. |
| 4,270,529 A | 6/1981 | Muto |
| 4,270,531 A | 6/1981 | Blachly |
| 4,351,331 A | 9/1982 | Gereg |
| 4,425,911 A | 1/1984 | Luomanen et al. |
| D283,158 S | 3/1986 | Jackson |
| 5,009,227 A | 4/1991 | Nieuwstad |
| 5,174,284 A | 12/1992 | Jackson |
| 5,390,661 A | 2/1995 | Griffith et al. |
| 5,413,095 A | 5/1995 | Weaver |
| 5,421,327 A | 6/1995 | Flynn et al. |
| 5,443,063 A | 8/1995 | Greenberg |
| 5,513,634 A | 5/1996 | Jackson |
| 5,590,643 A | 1/1997 | Flam |
| 5,620,408 A | 4/1997 | Vennes et al. |

(Continued)

FOREIGN PATENT DOCUMENTS

| | | |
|---|---|---|
| KR | 200395743 | 9/2005 |
| WO | WO 2007/067919 A2 | 6/2007 |
| WO | WO 2008/144768 | 11/2008 |
| WO | WO 2009/086277 A1 | 5/2009 |

OTHER PUBLICATIONS

U.S. Appl. No. 12/825,918 to Filipi, Office Action mailed Jul. 6, 2012.
Search Report and Written Opinion from PCT/US2008/064438.

(Continued)

*Primary Examiner* — Steven Douglas
(74) *Attorney, Agent, or Firm* — Woodard, Emhardt, Moriarty, McNett & Henry LLP

(57) ABSTRACT

Bite blocks providing an instrument lumen 62 for use during transoral medical procedures may be made from a material having a Shore D hardness less than 60 for improved patient comfort. An air way lumen 64 may be provide in side by side arrangement to the instrument lumen 62 for maintaining the patient's airway. The air way 70 may have a concave guiding channel 72 for helping to guide the instruments down the esophagus.

25 Claims, 7 Drawing Sheets

(56) References Cited

U.S. PATENT DOCUMENTS

| | | |
|---|---|---|
| 5,653,229 A | 8/1997 | Greenberg |
| 5,746,202 A | 5/1998 | Pagan |
| 6,244,865 B1 | 6/2001 | Nelson et al. |
| 6,257,238 B1 | 7/2001 | Meah |
| 6,361,540 B1 | 3/2002 | Gauderer et al. |
| 6,474,332 B2 | 11/2002 | Arndt |
| 6,517,549 B1 | 2/2003 | Dennis |
| 6,743,017 B2 | 6/2004 | O'Neill |
| 6,983,744 B2 | 1/2006 | Alfery |
| 7,077,841 B2 | 7/2006 | Gaiser et al. |
| 7,100,612 B2 | 9/2006 | Dunlap |
| 7,160,270 B2 | 1/2007 | West et al. |
| 7,171,962 B1 | 2/2007 | Bloem |
| 7,624,736 B2 | 12/2009 | Borody |
| 7,766,008 B2 | 8/2010 | Manishen |
| 7,934,505 B2 | 5/2011 | Garren et al. |
| 2002/0099387 A1 | 7/2002 | Gauderer et al. |
| 2002/0151871 A1 | 10/2002 | Gaiser et al. |
| 2003/0217744 A1 | 11/2003 | Sugai et al. |
| 2006/0149185 A1 | 7/2006 | Gaiser et al. |
| 2006/0272647 A1 | 12/2006 | Hauge |
| 2007/0006878 A1 | 1/2007 | Mackey et al. |
| 2007/0113844 A1 | 5/2007 | Garren et al. |
| 2007/0129735 A1 | 6/2007 | Filipi |
| 2008/0210232 A1 | 9/2008 | Trodler |
| 2008/0275473 A1 | 11/2008 | Filipi |

OTHER PUBLICATIONS

U.S. Appl. No. 12/825,918 to Filipi, Office Action mailed Aug. 29, 2013.

U.S. Appl. No. 12/825,918 to Filipi, Office Action mailed Jan. 30, 2014.

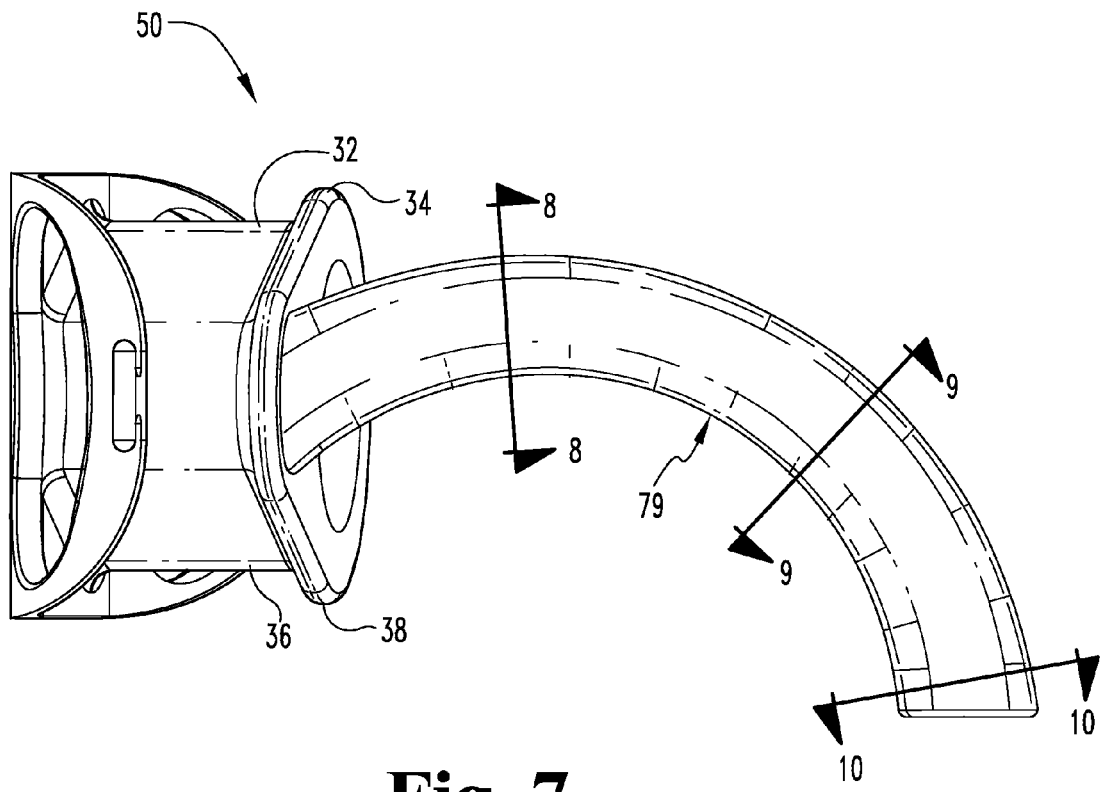
Fig. 7
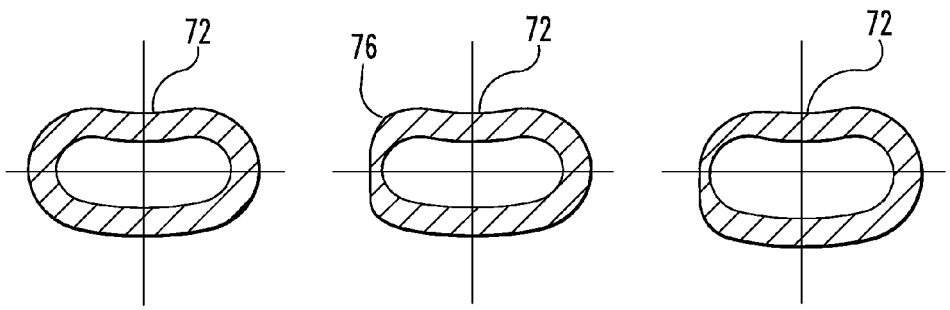
Fig. 8   Fig. 9   Fig. 10

BITE BLOCKS

RELATED APPLICATION DATA

This application is a continuation of PCT/US2008/64438 filed May 21, 2008, which claims the benefit of U.S. Provisional Application Ser. No. 60/939,348, filed May 21, 2007.

TECHNICAL FIELD

The present is generally related to bite blocks for use during surgical procedures. More particularly, but not exclusively, they related to novel bite blocks for use during transoral procedures.

BACKGROUND

Bite blocks are used in a variety of transoral procedures and generally serve to hold the patient's mouth open and provide an access path for surgical instruments. Commercially available bite blocks are typically held in position externally via a retaining strap placed around the patient's head. They also typically include a raised lip on their inside edge, which is positioned behind the patient's teeth and serves to prevent the bite block from being pushed beyond the teeth.

In order to provide an instrument lumen with sufficient rigidity to resist compression by the patient biting down on the block, which could cause damage to the instruments passing through device, commercially available bite blocks are typically molded from hard plastic materials, such as a high density polyethylene. The inherent strength of these materials allows the instrument lumen to be defined by a relatively thin shell of material, e.g. a wall thickness of about 2 mm, while providing adequate protection against the block being compressed by a biting force. However, such hard plastics can be uncomfortable for the patient. Moreover the overall height of the raised lip on these thin walled bite blocks can sometimes be inadequate to prevent expulsion of the bite block.

Furthermore, while conventional bite block designs providing a single instrument lumen have a variety of applications, they may not be ideal for all procedures. For example the characteristics of the surgical instruments and/or the nature of the patient may indicate a need to positively constrain not just the teeth, but other anatomical structures in and beyond the oral cavity, for example, the patient's tongue. As one example, it has been found that an unconstrained tongue in an obese patient's undergoing a transoral procedure, for example, a gastroplasty procedure as described in PCT/US2006/61665 filed Dec. 6, 2006 entitled SYSTEMS AND TECHNIQUES FOR MINIMALLY INVASIVE GASTROINTESTINAL PROCEDURES can sometimes result in airway constrictions or other complications.

Accordingly, there are needs for improvements in the art. In one form the present application provides improved bite block designs and methods of construction that address one or more of the needs outlined above.

BRIEF DESCRIPTION OF THE DRAWINGS

FIG. 7 is a side elevational view of the FIG. 5 bite block.
FIGS. 8, 9, and 10 show the cross sectional profiles along the length of the airway as indicated in FIG. 7.

DESCRIPTION

Figure 1:
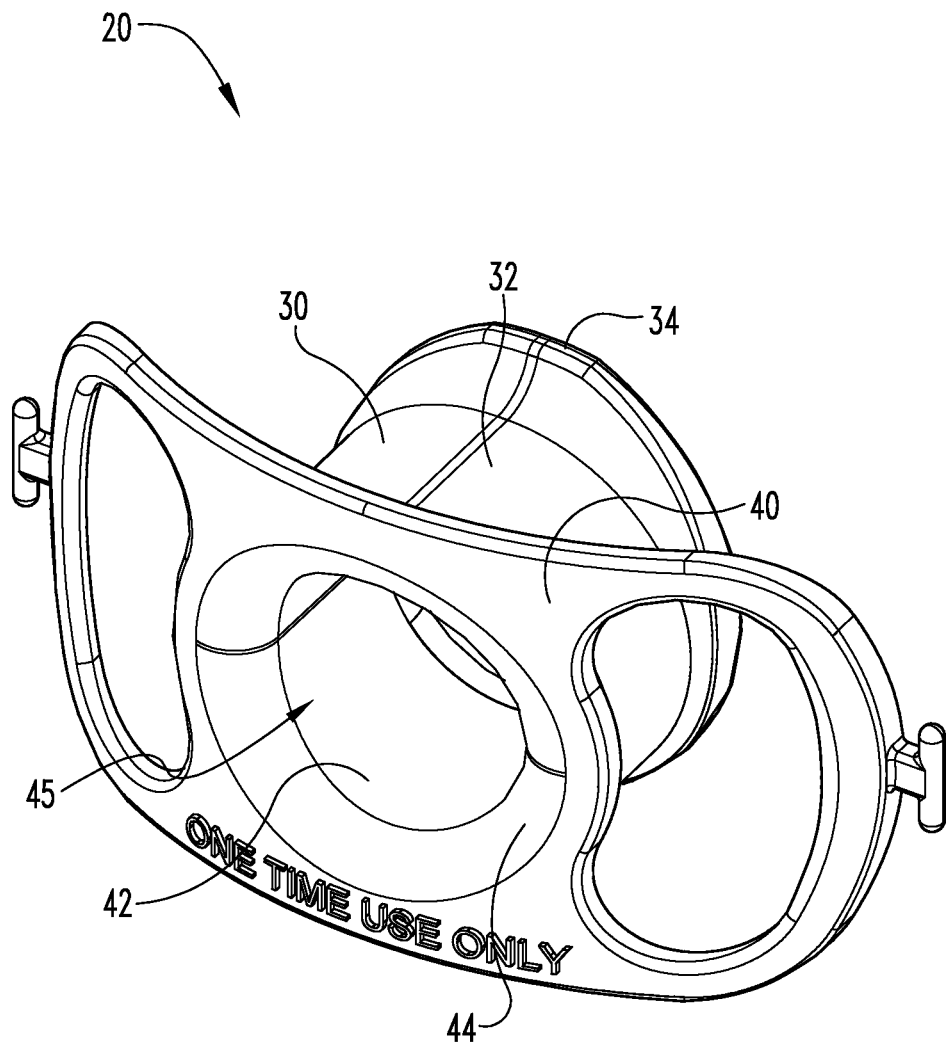
FIG. 1 is a perspective view of a bite block.

Referring now to FIGS. 1-4, a bite block 20 includes a main bite bock body 30 adapted to be positioned in a patient's mouth such that the upper and lower surfaces 32, 36 are facing the upper and lower teeth (not shown) respectively. Bite block 20 includes a front face 40 which is adapted to be outside the patient and upper and lower flanges 34, 38, which are adapted to be inside the patient's mouth just behind the upper and lower teeth (not shown).

The front face 40 of bite block 20 defines a front opening 45 to an instrument lumen 42. The instrument lumen 42 is sized to allow passage of surgical instruments, and may define an effective inner diameter of any useful size, for example at least about 20 mm or about 23.5 mm. In alternative implementations, the effective inner diameter may be in the range of 25-28 mm or about 27 mm. To facilitate passage of large diameter instruments, perimeter 44 of opening 45 is rounded with a relatively large radius of curvature, for example at least about 3 or 4 mm Front face 40 further defines side or wing openings 46, which are each sized to allow passage of a rigid tube having an outer diameter up to 14 mm. Such a tube may be used to provide suction during use. The side ends of the bite block 20 include a pair of fasteners 48 for connection to a head strap (not shown), which serves to secure the bite block in position. The fasteners 48 are illustrated as conventional T-shaped fasteners that may be coupled to a conventional elastic head strap.

Bite block 20 may be formed from any number of biocompatible or food grade synthetic or polymeric materials. The material may be selected such that bite block 20 may be formed by a conventional molding process, such as injection molding. Preferably, the material is selected to be relatively resilient plastic.

In one form, the bite block material has a Shore D Durometer hardness (calculated per ASTM D2240) less than 65, more typically in the range about 45 to about 60. In another form, the bite block material is a low density polymer mixture, for example having a density below 9.4 g/cm$^3$. One suitable material is Paxothene NA207-66 available from USI Corporation (Taipei, Taiwan), which is a low density polyethylene (LDPE) having a density of 0.921 g/cm$^3$ and a Shore D hardness of 53.

Figure 3:
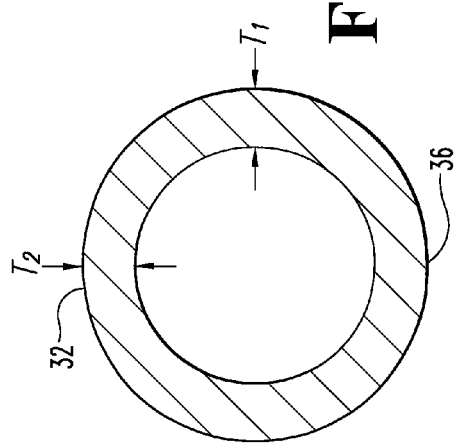
FIG. 3 shows the cross sectional profile as indicated in FIG. 2.
Figure 4:
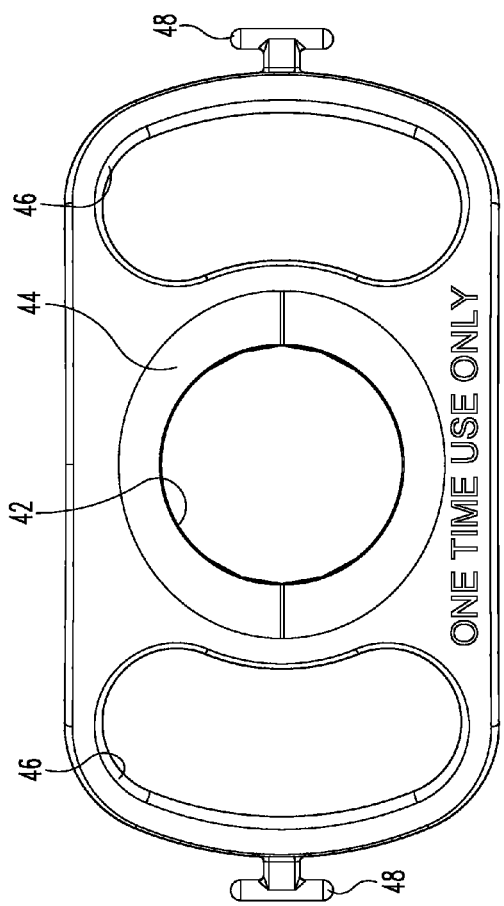
FIG. 4 is a front elevational view of the FIG. 1 bite block.
Figure 5:
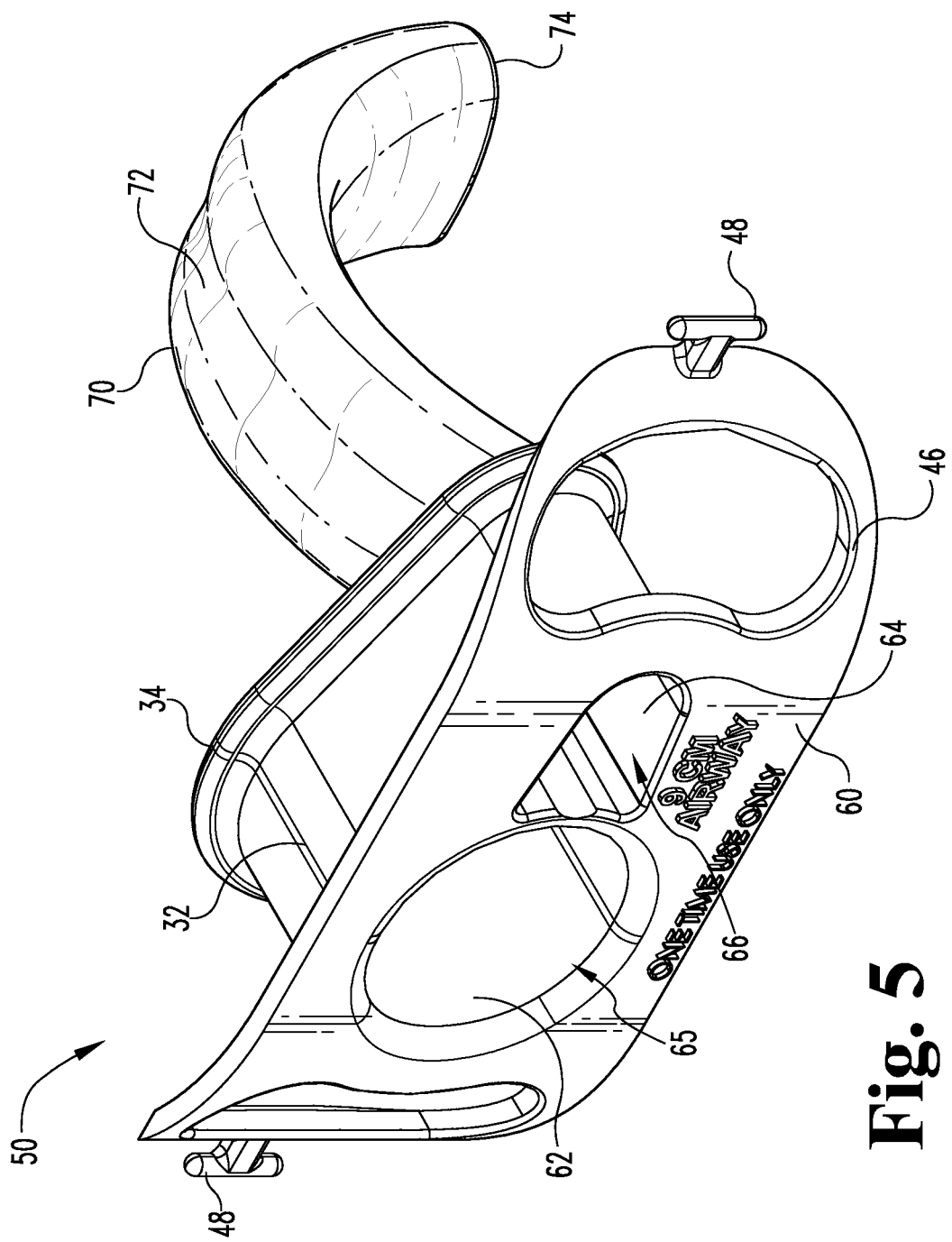
FIG. 5 is a perspective view of a combination airway bite block.
Figure 6:
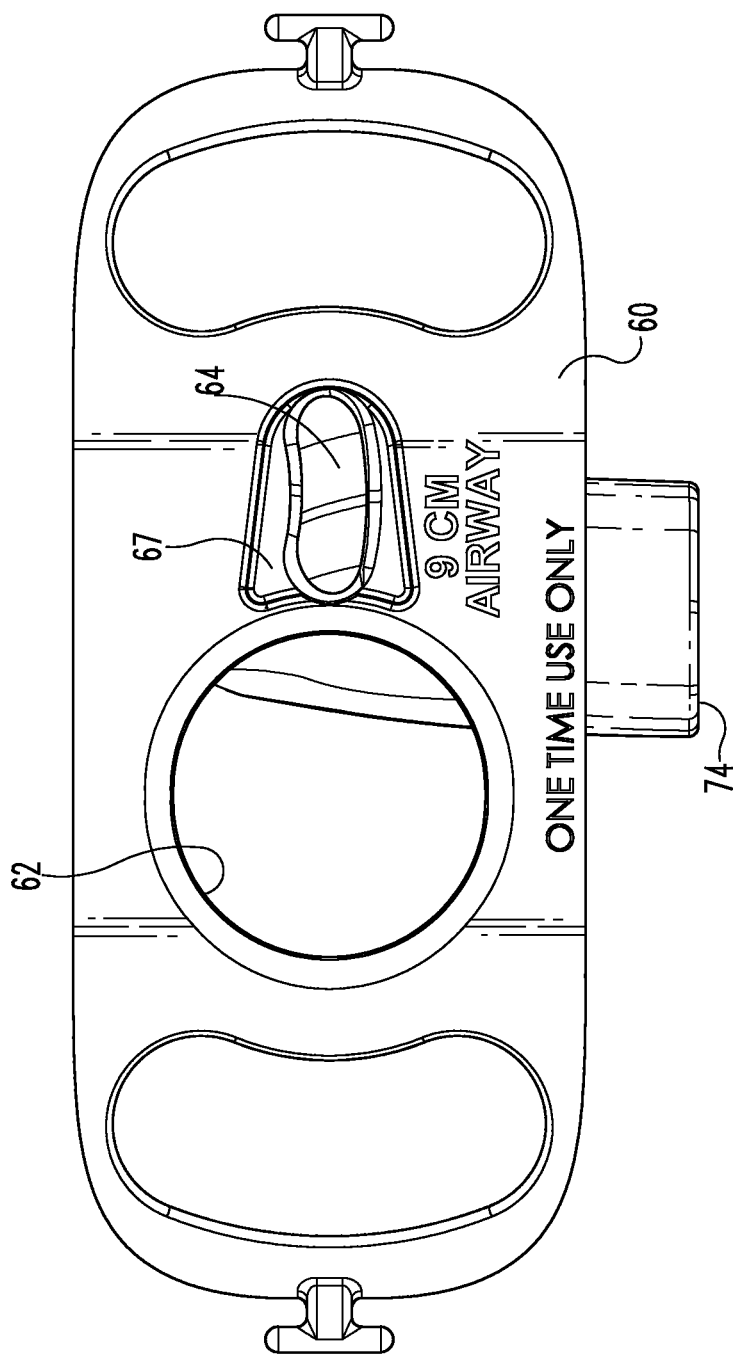
FIG. 6 is a front elevational view of the FIG. 5 bite block.
Figure 11:
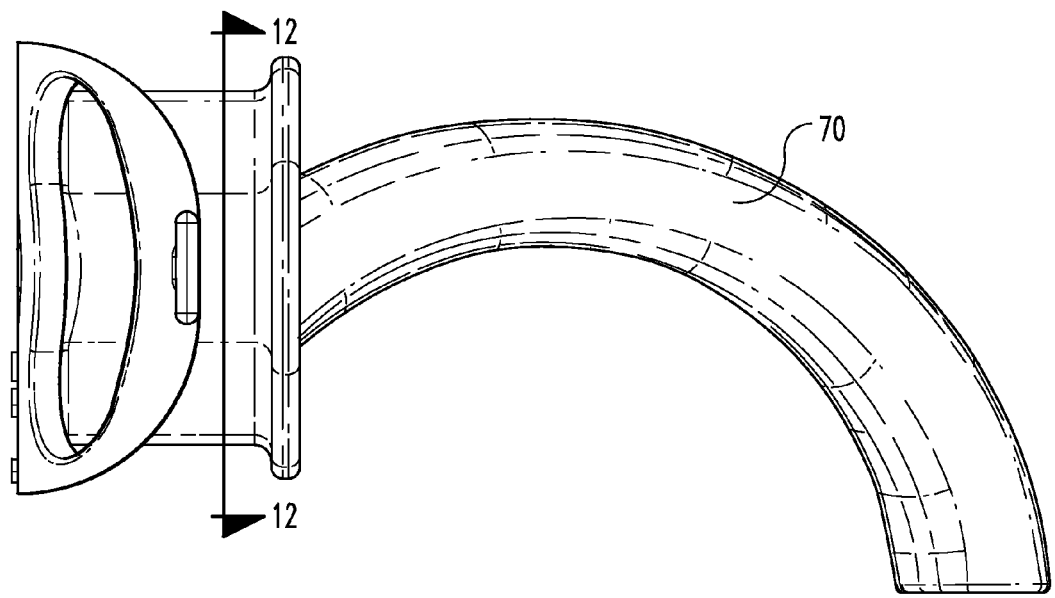
FIG. 11 is another side elevational view of the FIG. 5 bite block.
Figure 12:
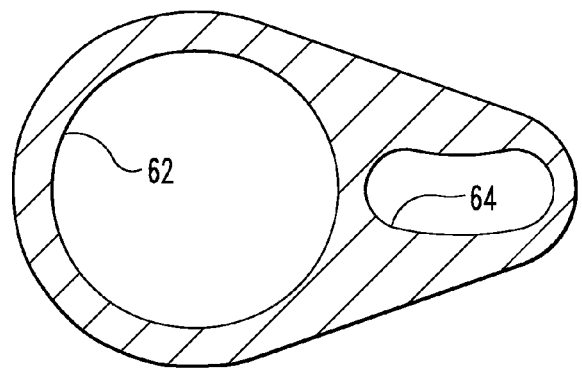
FIG. 12 shows the cross sectional profile as indicated in FIG. 11.

Referring to the cross sectional schematic depicted in FIG. 3, the side wall thickness $T_1$ and the upper and lower wall thickness $T_2$ are chosen such that the resulting structure resists compression under an applied bite load up to about 33 lbs. Such a compressive force may cause slight deformation to the inner dimensions, but preferably, block body 30 is designed such that the effective inner diameter of instrument lumen 42 is at least 20 mm under a bite load of about 30 lbs. For example $T_1$ and $T_2$ may be in the range of about 3-7 mm, for example, between 4-6 mm. In one implementation, $T_1$ is about 5.7 mm and $T_2$ is about 5.0 mm. In comparison, for conventional bite blocks constructed from high density polyethylene (HDPE), which would typically have a Shore D hardness above 65, a typical wall thickness may be only about 2 mm.

Figure 2:
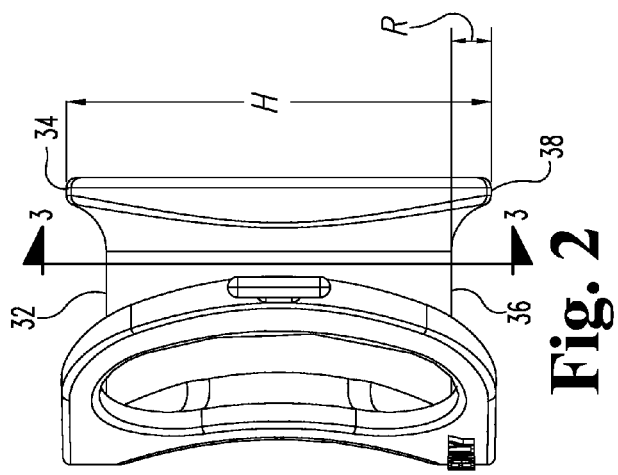
FIG. 2 is a side elevational view of the FIG. 1 bite block.

Upper and lower lip portions 34, 38 rise above the upper and lower surface portions 32, 36 to form a retaining flange or lip. With reference to FIG. 2, the rise R from the tooth landing to the top of a respective retaining lip is in the range of 3-5 mm, for example, about 4 mm. The overall height H of the retaining flange is preferably in the range of about 35 mm to about 45 mm, for example between 40 and 45 mm, for example about 41 mm. By comparison, known commercially available bite blocks have a slightly lower lip rise (R) and an overall retaining flange height (H) of around 31.5 mm. The larger overall height H makes it harder for the patient to expel the block, because the patient would need to open his mouth wider to clear the flange.

Referring now to FIGS. 5-13, another bite block 50 providing an instrument lumen 62 for transoral procedures is depicted. Bite Block 50 may be constructed of similar material and with similar dimensions as described above for bite block 20, but such dimensions and materials are not essential. Bite block 50, which may be called the obesity bite block, is intended for situations where, in addition to providing an instrument access path through the patient's mouth and into the esophagus, it is desirable to maintain an airway for the patient and/or otherwise exert positive control over the anatomy of the airway. For example, the tongues of morbidly obese patients can sometimes get in the way and make it difficult to maintain an adequate airway. In such situations, incorporation of an airway alongside the instrument access path can be advantageous.

As illustrated, the obesity bite block includes an airway lumen 64 alongside the operational lumen 62. Outer face 60 defines a main opening 65 that, like the opening 45 in bite block 20, is configured to allow instruments (e.g. dilators, endoscopes, not shown) to be inserted through block body and into the patient's esophagus. Adjacent the main opening 65, is airway opening 66, which serves as the entrance to airway lumen 64. Airway lumen 64 extends through the block body and continues distally past the lip flange 34 inside airway 70 and terminates at distal end 74.

Airway 70 is configured to function as an oral pharynx airway by positively maintaining at least a predetermined internal cross sectional area along its length sufficient for airflow, for example at least about 90 mm$^2$. As illustrated, airway opening 66 is of larger effective cross sectional area, and a back wall 67 serves to transition between the larger proximal section of airway lumen 64 and substantially kidney shaped profile of airway 70.

In operation, underside surface 79 of airway 70 may be positioned against tongue (not shown) to help maintain it in position. Instruments inserted through lumen 62 initially are alongside airway 70, and as they travel distally into the oral cavity they may transition to being generally over airway 70. To facilitate this transition and spatial arrangement, airway 70 is provided with a guiding channel 72. As illustrated, channel 72 is generally concave resulting in the kidney shape, and for consistency the channel 72 is provided along the entire length. It is to be understood that channel 72 may only be present near the distal end 74. The radius of curvature of channel 72 may generally correspond to the instruments being used, and may be for example around 5-10 mm.

Figure 13:
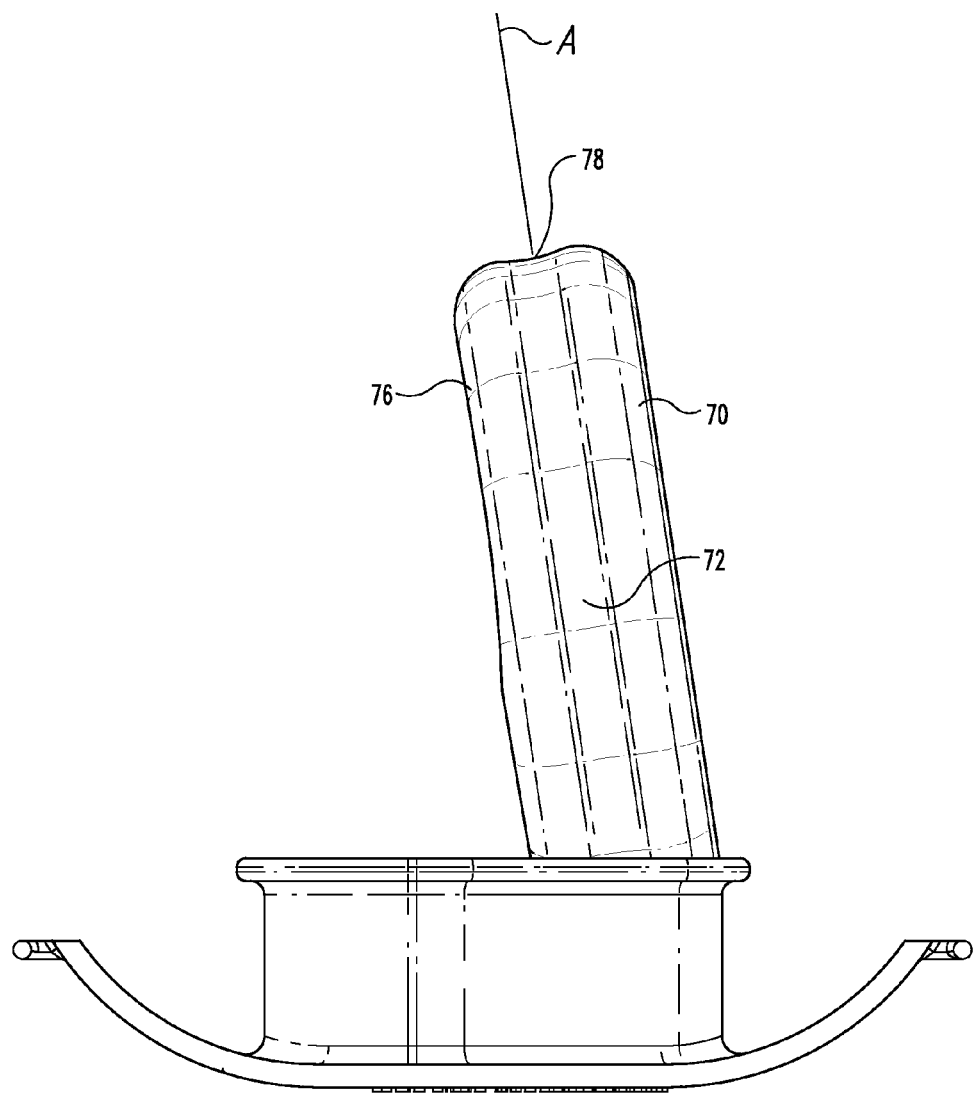
FIG. 13 is a top view of the FIG. 5 bite block.
Figure 14:
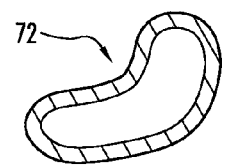
FIG. 14 shows the cross sectional profile for an alternative configuration for the airway.

Airway 70 is a smoothly curved body that generally lies in a vertical plane indicated by axis line A in FIG. 13, which makes an angle of about 10 degrees with the longitudinal axis of instrument lumen 62 (not shown). The objective of this arrangement is to orient airway 70 such that the guiding channel 78 is generally centered in the esophagus and can be used to help guide the passage of instruments (not shown) centrally down the esophagus. While the guiding channel 78 is generally centrally located along airway 70 as viewed in FIG. 13, asymmetrical arrangement are also contemplated. FIG. 14 depicts one potential arrangement for guiding channel 72 wherein the left lobe of the kidney is effectively reduced in size to promote a more size by side arrangement.

As depicted in FIGS. 7-10, a thinned wall section 76 may also be provided along the instrument side of the airway 70. This serves as an alternative mechanism for promoting the transition of the instrument from along side to on top of the airway 70.

It is to be appreciated that what has been described is a novel bite block for use during a transoral medical procedure, comprising a main bite block body defining upper and lower outer surfaces adapted to be positioned between a patient's upper and lower teeth respectively and defining an operating lumen for providing instrument access, wherein the bite block includes an outer face adapted to be positioned outside the patient's mouth during use, wherein upper and lower retention flange portions extend from the upper and lower outer surfaces so as to be positioned behind the patient's teeth during use, wherein the main bite block body comprises a polymeric material having a density below 9.4 g/cm$^3$ and Shore D Durometer hardness less than about 60, and/or wherein the effective inner diameter of the operating lumen is at least about 20 mm, and/or wherein the distance between the uppermost and lowermost portions of the retention flange portions is between 35 mm and 45 mm. The main bite block body may be constructed such that the effective inner diameter of the operating lumen is at least 20 mm under a bite load of about 30 lbs. The wall thickness of the main bite block body about the operating lumen may be between 4 and 6 mm. The main bite block body may comprise a low density polymer such as polyethylene and the like. The outer face of the bite block may define a first opening comprising the entrance to operating lumen and a second opening comprising the entrance to an oral pharyngeal airway, which may be formed integrally with the main bite block body. The construction of the airway may be such that it comprises an outer surface that defines a generally concave channel extending at least partially along the length of the airway and or wherein a cross sectional profile of the airway is generally kidney shaped. The axial center of a substantial portion of the airway may define a plane that is not parallel to a longitudinal axis defined by operating lumen, for example forming an angle of between 5 and 20 degrees, such as about 10.

What has also been described is A bite block and airway device comprising: a bite block body defining upper and lower outer surfaces adapted to be positioned between a patient's upper and lower teeth respectively; and an outer face piece of the device adapted to be positioned outside the patient's mouth during use, the outer face piece adapted to be coupled to a head strap; wherein the outer face piece defines first and second side by side openings comprising the entrance to an instrument lumen and an airway lumen respectively, wherein the lumens are located between the upper and lower surfaces of the body. The face piece may further define a pair of wing openings, which may be configured to allow passage of a rigid tube having an outer diameter up to about 14 mm. One or all of the components may be of unitary construction. The effective diameter of the instrument lumen may be about 20 mm and the effective cross sectional area of the airway lumen may be at least about 90 mm$^2$. The instrument lumen is configured such that it terminates inside the patient's mouth. The airway lumen may be configured such that it extends through the patient's oral cavity. A housing defining an oral pharynx airway adapted to extend through the patient's oral cavity may be provided. The housing may define an outer surface the airway comprises an outer surface that defines a generally concave channel extending at least partially along a distal length of the airway.

What has also been described is a bite block for maintaining a patient's airway during a transoral medical procedure, the bite block comprising: a main bite block body defining upper and lower outer surfaces adapted to be positioned between the patient's upper and lower teeth respectively; wherein the main bite block body further defines an instrument lumen and an airway lumen in side by side arrangement between the upper and lower outer surfaces; wherein the instrument lumen is configured to accommodate passage of one or more surgical instruments and terminates distally in the oral cavity; wherein the airway lumen is configured to extend distally through the oral cavity. A substantial portion of the airway may be provided by a structure having a lower curvilinear surface adapted to be in contact with the tongue. The main bite block body may have a Shore D Durometer hardness less than about 60, and one or all components may be of unitary construction.

While the inventions have been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof.

What is claimed is:

1. A bite block for use during a transoral medical procedure, comprising
    a main bite block body defining upper and lower outer surfaces adapted to be positioned between a patient's upper and lower teeth respectively and defining an operating lumen for providing instrument access;
    wherein the bite block includes an outer face adapted to be positioned outside the patient's mouth during use;
    wherein upper and lower retention flange portions extend in a direction substantially perpendicular from the upper and lower outer surfaces, respectively, so as to be positioned behind the patient's teeth during use, wherein the upper and lower retention flange portions extend between about 3 to 5 millimeters from the upper and lower outer surfaces, respectively;
    wherein the outer face of the bite block defines a first opening comprising the entrance to an operating lumen and a second opening comprising the entrance to an oral pharyngeal airway, the airway having a length such that the airway extends through the patient's oral cavity;
    wherein the main bite block body comprises a polymeric material having a density below 9.4 g/cm$^3$ and Shore D Durometer hardness less than about 60;
    wherein the effective inner diameter of the operating lumen is at least about 20 mm; and
    wherein the distance between the uppermost and lowermost portions of the retention flange portions is between 35 mm and 45 mm.

2. The bite block of claim 1 wherein the distance between the uppermost and lowermost portions of the retention flange portions is greater than 40 mm.

3. The bite block of claim 1 wherein the main bite block body is constructed such that the effective inner diameter of the operating lumen is at least 20 mm under a bite load of about 30 lbs.

4. The bite block of claim 3 wherein the wall thickness of the main bite block body about the operating lumen is between 4 and 6 mm.

5. The bite block of claim 1 wherein the main bite block body comprises a low density polyethylene.

6. The bite block of claim 1 wherein the airway is formed integrally with the main bite block body.

7. The bite block of claim 1 wherein the airway comprises an outer surface that defines a generally concave channel extending at least partially along the length of the airway.

8. The bite block of claim 7 wherein a cross sectional profile of the airway is kidney shaped.

9. The bite block of claim 7 wherein the channel is adapted to guide an instrument centrally down the esophagus.

10. The bite block of claim 1 wherein the axial center of a substantial portion of the airway defines a plane that makes an angle of between 5 and 20 degrees with the longitudinal axis defined by the operating lumen.

11. A bite block and airway device comprising:
    a bite block body defining upper and lower outer surfaces adapted to be positioned between a patient's upper and lower teeth respectively;
    an outer face piece of the device adapted to be positioned outside the patient's mouth during use, the outer face piece adapted to be coupled to a head strap; and
    wherein the outer face piece defines first and second side by side openings comprising the entrance to an instrument lumen and an airway lumen respectively, wherein the lumens are located between the upper and lower surfaces of the body, wherein the airway lumen has a length that spans between a proximal end adjacent the bite block body and a distal end opposite the proximal end, the airway lumen configured to extend through the patient's oral cavity, the airway lumen having a guiding channel positioned on an outer surface of the airway lumen, wherein the cross-sectional area of the airway lumen opening is larger than the cross-sectional area of the airway lumen.

12. The device of claim 11 wherein the face piece further defines a pair of wing openings.

13. The device of claim 12 wherein the wing openings are each configured to allow passage of a rigid tube having an outer diameter up to about 14 mm.

14. The device of claim 11 wherein the bite block body and the face piece are of unitary construction.

15. The device of claim 11 wherein the effective diameter of the instrument lumen is at least about 20 mm and wherein the effective cross sectional area of the airway lumen is at least about 90 mm$^2$.

16. The device of claim 11 wherein the instrument lumen is configured such that it terminates inside the patient's mouth.

17. The device of claim 16 further comprising a housing defining an oral pharynx airway adapted to extend through the patient's oral cavity.

18. The device of claim 17 wherein the guiding channel has a concave shape.

19. The device of claim 18 wherein the housing is molded integrally with the bite block body.

20. A bite block for maintaining a patient's airway during a transoral medical procedure, the bite block comprising:
- a main bite block body defining upper and lower outer surfaces adapted to be positioned between the patient's upper and lower teeth respectively;
- wherein the main bite block body further defines an instrument lumen and an airway lumen in side by side arrangement between the upper and lower outer surfaces, the instrument lumen having a longitudinal axis, wherein an axial center of a substantial portion of the airway lumen defines a plane that forms an angle of between 5 and 20 degrees with the longitudinal axis of the instrument lumen;
- wherein the instrument lumen is configured to accommodate passage of one or more surgical instruments and terminates distally in the oral cavity; and
- wherein the airway lumen is configured to extend distally through the oral cavity.

21. The bite block of claim 20 wherein the airway includes a structure having a lower curvilinear surface adapted to be in contact with the tongue, the structure also having an upper outer surface adapted to guide one of the surgical instruments down the patient's esophagus.

22. The bite block of claim 21 wherein the main bite block body has a Shore D Durometer hardness less than about 60.

23. The bite block of claim 22 wherein the main bite block body and the structure are of unitary construction.

24. The device of claim 11 further comprising:
- an upper retention flange positioned on the upper outer surface, the upper retention flange having a height and a thickness; and
- a lower retention flange positioned on the lower outer surface, the lower retention flange having a height and a thickness.

25. The device of claim 20 further comprising:
- an upper retention flange positioned on the upper outer surface, the upper retention flange having a height and a thickness; and
- a lower retention flange positioned on the lower outer surface, the lower retention flange having a height and a thickness, wherein the upper and the lower retention flanges are adapted to be positioned between the patient's upper and lower teeth respectively.

\* \* \* \* \*